United States Patent [19]

Young et al.

[11] 4,352,833

[45] Oct. 5, 1982

[54] ADHERENT CONTROLLED RELEASE PESTICIDES

[75] Inventors: Robert W. Young, New York, N.Y.; Samuel Prussin, Carmel, Calif.; Norman G. Gaylord, New Providence, N.J.

[73] Assignee: Young, Prussin, MGK, J.V., New York, N.Y.

[21] Appl. No.: 272,788

[22] Filed: Jun. 11, 1981

Related U.S. Application Data

[63] Continuation of Ser. No. 102,638, Dec. 12, 1979, abandoned, which is a continuation of Ser. No. 858,603, Dec. 8, 1977, abandoned, which is a continuation of Ser. No. 696,271, Jun. 15, 1976, abandoned.

[51] Int. Cl.$^3$ .................. A61K 31/695; A01N 17/08
[52] U.S. Cl. ........................................ 427/4; 424/184; 424/186
[58] Field of Search .................. 427/2, 4; 424/77, 78, 424/184, 186, DIG. 10, DIG. 6; 71/DIG. 1, DIG. 2; 43/136

[56] References Cited

U.S. PATENT DOCUMENTS

| | | | |
|---|---|---|---|
| 2,681,878 | 6/1954 | Kaupp | 424/184 |
| 2,988,473 | 6/1961 | Mallis | 424/184 |
| 3,151,969 | 10/1964 | Stevens | 424/186 |
| 3,480,653 | 11/1969 | Pande | 260/429.9 |

*Primary Examiner*—Sam Silverberg
*Attorney, Agent, or Firm*—Roylance, Abrams, Berdo & Farley

[57] ABSTRACT

There are disclosed methods and compositions for the controlled release of insecticides by using a mixture consisting of (a) a solid polysiloxane containing hydroxyl groups, and (b) a pesticide, e.g., an insecticide.

15 Claims, No Drawings

ADHERENT CONTROLLED RELEASE PESTICIDES

This is a continuation of application Ser. No. 102,638, filed Dec. 12, 1979, now abandoned, which is a continuation of application Ser. No. 858,603, filed Dec. 8, 1977, now abandoned, which is a continuation of application, Ser. No. 696,271, filed June 15, 1976, now abandoned.

This invention relates to methods and compositions for the controlled release of bioactive agents and, more particularly, to the controlled release of pesticides, such as insecticides.

The utilization of bioactive agents such as pesticides, e.g., insecticides, herbicides and fungicides has become an important fact of life. However, these materials are generally effective only as long as they persist on the substrate to which they are applied.

The basic motivation underlying the modern development of controlled release pesticidal materials has been to extend the duration between applications and thus increase the efficiency and hence economy of control. Controlled release of pesticides permits extended time intervals between treatments and reduction of the dosage, thus reducing environmental impact. Thus, from an ecological standpoint, controlled release of pesticides enhances the lifetime of a non-persistent agent at the site of treatment while maintaining the preferred property of rapid detoxification in the environment surrounding the controlled release pesticide.

The desired controlled release of pesticides has previously been achieved by their incorporation within a polymeric matrix, e.g., encapsulation wherein a pest control agent is surrounded by an enveloping polymeric wall that permits loss through diffusion, permeation or degradation; dispersion of the pesticide in an elastomer or a plastic wherein the pesticide is released through leaching or diffusion; and the chemical combination of the pesticide with a polymer in such a manner that the appended pesticide slowly breaks off the polymeric backbone upon exposure to the pest infested environment. However, the prior art approaches fall short of the desired goal in that there is not adequate provision for the adhesion of the pesticide within the polymeric matrix to the substrate. This permits the removal or transfer of the material from the substrate as a result of physical contact, wind, rain or other atmospheric conditions.

One object of the present invention is to provide a process for the controlled release of bioactive agents such as pesticides.

Another object of the present invention is to improve the adhesion of such an agent to suitable substrates and thus to increase its effective lifetime.

Another object of the present invention is to provide stable compositions which after application to a sutable substrate and exposure to the atmosphere, form solid, adherent flims resulting in adherent insecticides with controlled release characteristics.

A further object of the present invention is to provide novel compositions containing solid, hydroxyl containing polysiloxanes, and insecticides.

These and other objects of the present invention are achieved by using a mixture consisting of (a) a solid polysiloxane containing hydroxyl groups, and (b) an insecticide.

The organopolysiloxanes suitable for use in the practice of the present invention are well known in the art and contain the structural unit

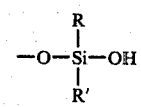

wherein R and R' are oxygen (i.e., the group —O—), hydrogen, hydrocarbon, substituted hydrocarbon or heterocyclic radicals and are the same or different. When R and R' are hydrocarbon radicals, they may be acyclic or cyclic, saturated or unsaturated and include aliphatic radicals such as methyl, ethyl, vinyl, propyl, allyl, butyl, crotyl, hexyl, decyl, dodecyl, hexadecyl, octadecyl, octadecenyl radicals and the like as well as halogenated or other substituted aliphatic radicals, aromatic radicals such as phenyl, biphenyl, phenoxyphenyl and naphthyl radicals as well as halogenated and other substituted aromatic radicals, aralkyl radicals such as benzyl and phenylethyl radicals, alkylaryl radicals such as tolyl and xylyl radicals, cycloalphatic radicals such as cyclopropyl, cyclopentyl, cyclopentenyl, cyclohexyl and cyclohexenyl radicals and heterocyclic radicals such as furfuryl radicals.

The organopolysiloxanes may be linear, branched or both linear and branched and the hydroxyl radicals may be terminal end groups or may be situated at other sites in the polysiloxane chain. The number of hydroxyl radicals may range from one radical per polysiloxane molecule up to 30 weight percent of the total organopolysiloxane molecular weight.

The polysiloxane may be predominantly a monoorganopolysiloxane, a diorganopolysiloxane, a copolymer containing monoorganosiloxane units and diorganosiloxane units, a copolymer containing triorganosiloxane units and SiO₂ units and the like. Notwithstanding the predominant structure, the organopolysiloxane may contain varying amounts of the other structural units in addition to hydroxyl radicals.

The polysiloxanes suitable for use in the practice of the present invention are well known in the art and may be prepared by various procedures including controlled hydrolysis of appropriate precursors as well as ring opening polymerization of cyclic organopolysiloxanes.

The controlled hydrolysis and cohydrolysis of $RSiX_3$, $R_2SiX_3$, $R_3SiX$ and $SiX_4$, where X is a hydrolyzable radical such as alkoxy, acyloxy, hydrogen, halogen and the like, yields organopolysiloxanes containing monoorganosiloxane, diorganosiloxane, triorganosiloxane and SiO₂ units, respectively. The relative proportions of said units in the organopolysiloxane are determined by employing the appropriate ratios of hydrolyzable precursors. In order to be useful in the practice of the present invention, the resultant organopolysiloxane must be solid, readily soluble or dispersible in organic solvents and contain residual hydroxyl radicals.

The polymerization of cyclic organopolysiloxanes provides another route to the preparation of organopolysiloxanes containing hydroxyl radicals which may be employed in the practice of the present invention. These and other methods of preparation are set forth in K. A. Andrianov, "Metalorganic Polymers", Interscience Publishers, New York, 1965, Chapter III, pages 109–275, the disclosures of which are incorporated herein by reference.

Polysiloxanes which are at an intermediate stage of polymerization in that they contain hydroxyl radicals which, upon application of heat, may undergo condensation to a more advanced stage of polymerization, are suitable for use in the practice of the present invention if they are solid and have not been rendered insoluble in organic solvents. Mixtures of solid polysiloxanes are suitable for use in the present invention.

Insecticides which may be used in the practice of this invention include any of the compounds well known in the art for use as insecticides such as those set forth in Chemical Week, June 21, 1972, pages 39–64; Chemical Week, July 26, 1972, pages 19–41; and Commercial and Experimental Organic Insecticides (1974 Revision), Entomological Society of America, Special Publication 74-1, October 1974. Some common insecticides which may be used include the following:

1-naphthyl methylcarbamate (SEVIN)
malathion
methylparathion
toxaphene
Dursban
DDT
pyrethrins
parathion
phorate
chlordane
Baygon
Diazinon The insecticides which may be used in the practice of this invention also include bacterial insecticides such as *Bacillus popilliae* and *Bacillus thuringiensis* and viral insecticides such as the Heliothis virus. These have been described in Chemical & Engineering News, 35, No. 30, 18 (July 28, 1975), the disclosures of which are incorporated herein by reference.

The insecticide is included in the composition in an amount sufficient to exert an insecticidal action on the immediate environment surrounding the substrate. The amount of insecticide will be dependent upon several factors such as the composition and thickness of the polymeric martix, the nature of the insecticide, i.e., liquid or solid, the duration of insecticidal action desired, etc. The optimum amount of insecticide to be included may readily be determined by those skilled in the art. Generally, from about 1 part by weight of insecticide to 0.5 to 1000 parts of the weight of solid polysiloxane is satisfactory.

The compositions of this invention may include volatile diluents such as aliphatic or aromatic hydrocarbons, e.g., Stoddard Solvent, mineral spirits, B & P nahtha, cyclohexane, petroleum ether, benzene, toluene, xylene, etc., halogenated hydrocarbons such as perchloroethylene and fluorocarbons or volatile fluid polysiloxanes such as dimethylpolysiloxane fluids. The compositions may be prepared by merely admixing the various components. Before mixing, the components may be dispersed or dissolved in a diluent such as previously described. The compositions may also be prepared in aqueous media.

The compositions of this invention may be applied to a large number of substrates. The substrate should be one which contains active hydrogen atoms which provide sites for hydrogen bonding with the polysiloxane hydroxyl groups, e.g., hydroxyl groups, amino groups, etc. Thus, various plants such as ornamental bushes, trees, flowers, greenhouse plants, lawns, crops (e.g., wheat, corn, soy beans, barley, oats, cotton, jute, sisle), fruits, vegetables, berry bushes, nut trees, olive trees, fig trees, grape vines; various animals such as household pets (e.g., cats, dogs), farm animals such as dairy cattle, beef cattle, horses, sheep, chickens, turkeys, swine, goats, zoo animals, etc. Non-plant and animal uses include spraying surfaces of structures such as buildings and various rooms in buildings, such as kitchens, bathrooms, closets including wood or plaster board walls and floor tile to protect against roaches, termites, flying insects, rug insects, ants, etc. Various containers such as bags and cardboard or wooden boxes may also serve as substrates in accordance with the practice of this invention.

The compositions of this invention may be applied to the substrate by brushing, spraying, dipping or any other known technique for applying a fluid composition to a solid substrate. It may be applied in the form of an aerosol mist or fog, propelled by conventional pressurized volatile halohydrocarbon, hydrocarbon or compressed gas propellants, an air propelled mist blower, a fog generator, or other suitable means.

Upon application of the compositions of this invention to a suitable substrate, evaporation of the volatile diluent results in the formation of a solid polysiloxane coating containing entrapped or occluded insecticide. The adhesion of the polysiloxane and the insecticide therein to the substrate is due at least in part to the fact that the polysiloxane matrix is coupled to the substrate by hydrogen bonding between the polysiloxane hydroxyl groups and the active hydrogen atoms on the substrate. In this manner, the insecticide is held on the substrate to such an extent that it cannot be physically brushed off, blown off or washed off by rain. Further, as a result of its entrapped condition the rapid evaporation, sublimation or extraction of the insecticide is retarded. However, due to the permeability of the polysiloxane to organic compounds, said evaporation or sublimation is not completely inhibited, resulting in controlled release of the insecticide.

The rate of release of the insecticide may be controlled by adjusting the thickness of the polysiloxane coating, e.g., by modifying the concentration of components in the composition, or by adding a non-volatile, non-reactive extender for the polysiloxane. The latter may be a hydrocarbon oil and acts in a manner analogous to the behavior of the hydrocarbon oil in a vulcanized oil-extended hydrocarbon rubber. The extender may be a compatible non-siloxane compound e.g., a hydrocarbon oil or may be an alkyl or arylpolysiloxane fluid having a viscosity ranging from 5 to 100,000 centistokes at 25° C.

Other additives which may be incorporated into the compositions of this invention include stabilizers against environmental degradation, such as antioxidants and ultraviolet stabilizers, odor masking compounds and perfumes, dyes, pigments, fillers, etc.

The following examples illustrate the best mode for carrying out this invention. Example I illustrates the improved adhesion of the compositions of this invention to a substrate. In the tables, the numbers refer to the amount of material in parts by weight.

EXAMPLE I

A. Solutions containing 50 weight-% of one of the following hydroxyl-containing polysiloxanes were prepared in anhydrous isooctane: (1) a liquid, linear dimethylpolysiloxane containing 3 weight-% hydroxyl groups, designated as F1-3563 by the Dow Corning Corp., (2) a solid, branched siloxane copolymer composed of trimethylsiloxy units and $SiO_2$ units, with a $CH_3/Si$ ratio of 1.4, containing 3 weight-% hydroxyl groups, designated as X2-5056 by the Dow Corning Corp., and (3) a solid, branched propylphenylpolysiloxane containing 6 weight-% hydroxyl groups, designated as Z-6018 by the Dow Corning Corp.

B. Solutions containing 50 weight-% of one of the following non-reactive liquid polysiloxanes were prepared in anhydrous isooctane: (1) a liquid dimethylpolysiloxane, designated as a DC-200 fluid by the Dow Corning Corp., having a viscosity of 1000 centistokes at 25° C. (DC-200/1000), (2) a liquid methylphenylpolysiloxane containing 50 mole-% phenyl groups, having a viscosity of 115 centistokes at 25° C., designated as DC-550 fluid by the Dow Corning Corp.

C. Solutions containing 50 weight-% of a mixture of one of the liquid or solid hydroxyl-containing polysiloxanes of (A) with one of the liquid polysiloxanes of (B) were prepared in anhydrous isooctane.

The 50% solution was diluted to 10 weight-% with isooctane and 10–20 drops were placed on a weighed glass slide. A glass rod was rolled over the solution to spread the material uniformly over the lower four fifths of the slide. The coated slide was air dried for four hours and then placed in a 50% relative humidity chamber for 18 hours. The slide was then weighed to determine the weight of the coating which ranged from 2-5 mg., covering an area of 15 sq. cm. The coated slide was inserted into a slit rubber stopper and mounted over the center of a Waring Blender. The coated slide faced the moving water which completely covered the coating. The blender was operated at its highest speed for 5 minutes. The slide was air dried overnight and then weighed to determine the amount of coating retained on the slide after the treatment in the Blender. The averaged results of duplicate tests are sumarized in Table 1.

TABLE 1

Adhesion of Silanol Compositions

| No. | Silanol F1-3563 (liquid) | X2-5056 (solid) | Z-6018 (solid) | DC-200/ 1000 | DC-550 | Retention, % |
|---|---|---|---|---|---|---|
| 1 | | | | 100 | | 44 |
| 2 | 100 | | | | | 28 |
| 3 | 50 | | | 50 | | 15 |
| 4 | | 100 | | | | 100 |
| 5 | | 50 | | 50 | | 90 |
| 6 | | | | | 100 | 8 |
| 7 | | | 100 | | | 96 |
| 8 | | | 50 | | 50 | 79 |

The retention of the solid silanol is practically complete while the liquid silanol is readily removed. The presence of the liquid polysiloxane fluid only reduced the retention of the solid silanol to a small extent.

The 50% solutions of liquid silanol F1-3563, solid silanol X2-5056 and the mixtures thereof with DC-200/1000 polysiloxane fluid in isooctane were mixed with a pyrethroid composition as follows:
  0.1 g. pyrethroids
  0.5 g. piperonyl butoxide
  0.4 g. petroleum distillate
  5.0 g. 50% solution of F1-3563, X2-5056 and/or DC 200/1000 in isooctane The pyrethroid-containing solutions were diluted to 10 weight-% with isooctane and coated on glass slides. The coated slides were dried, moisture cured and subjected to treatment with water in the Waring Blender, as described earlier. The amount of retained coating is summarized in Table 2, where the amount of pyrethroids indicated actually represents the sum of the pyrethroids and piperonyl butoxide.

TABLE 2

Adhesion of Pyrethroid-Silanol Compositions

| No. | Silanol F1-3563 (liquid) | X2-5056 (solid) | DC-200/1000 | Pyrethroids | Retention, % |
|---|---|---|---|---|---|
| 9 | | | 100 | 24 | 4 |
| 10 | 100 | | | 24 | 0 |
| 11 | 50 | | 50 | 24 | 2 |
| 12 | | 100 | | 24 | 90 |
| 13 | | 50 | 50 | 24 | 85 |

The presence of the pyrethroids has little effect on the retention of the solid silanol while the poor retention of the liquid silanol is made even worse.

EXAMPLE II

A solution containing 5 weight-% non-volatiles was prepared as follows:
  1.5 g. solid propylphenylpolysiloxane Z-6018 (6 wt-% OH)
  1.5 g. DC-550 methylphenylpolysiloxane fluid
  57.0 g. perchloroethylene The solid polysiloxane Z-6018-polysiloxane fluid solution was mixed with a pyrethroid composition to yield an insecticide-containing solution which was compared with an additive-free pyrethroid composition for insecticidal behavoir. The components of the test compositions were as follows:

| | Insecticide Solution | |
|---|---|---|
| | IIA | IIB |
| Pyrethroids | 0.1 | 0.1 |
| Piperonyl butoxide | 0.5 | 0.5 |
| Petroleum distillate | 0.4 | 0.4 |
| Z-6018 | 2.45 | — |
| DC-550 | 2.45 | — |
| Perchloroethylene | 94.1 | 99.0 |

A disposable plastic syringe was used to place the test solution on a 4×4 inch glass panel. The solution was uniformly spread over the panel with the tip of the syringe. The treated panels were conditioned for 24 hours in a chamber at 78° F. and 42% relative humidity. Ten adult male German cockroaches, Blattella germanica (Linnaeus), were exposed to the 1 day residue for 24 hours under a 100×15 mm. petri dish. The test was conducted in duplicate. The same treated panels were reexposed to cockroaches after 3, 7 and 10 days.

The percent mortality of cockroaches exposed to the treated glass panels is summarized below:

| | Insecticide Solution | |
|---|---|---|
| Residue Age | IIA | IIB |
| 1 day | 100 | 100 |
| 3 days | 100 | 100 |
| 7 days | 80 | 15 |
| 10 days | 10 | 0 |

The residue from the control insecticide solution IIB killed 15% of the exposed cockroaches after 7 days while the residue from insecticide solution IIA, containing the solid polysiloxane-polysiloxane fluid mixture, killed 80% of the exposed cockroaches after 7 days and 10% after 10 days.

EXAMPLE III

A solution containing 50 weight-% non-volatiles was prepared as follows:
  30 g. solid polysiloxane copolymer X2-5056 (3wt-% OH)
  30 g. perchloroethylene The polysiloxane copolymer solution was mixed with a pyrethroid composition to yield an insecticide-containing solution which was compared with an additive-free pyrethroid composition for insecticidal behavior. The components of the test compositions were as follows:

|  | Insecticide Solution | | | |
| --- | --- | --- | --- | --- |
|  | IIIA | IIIB | IIIC | IIID |
| Pyrethroids | 0.1 | 0.1 | 0.1 | 0.1 |
| Piperonyl butoxide | 0.5 | 0.5 | 0.5 | 0.5 |
| Petroleum distillate | 0.4 | 0.4 | 0.4 | 0.4 |
| X2-5056 | 2.5 | 1.0 | 0.5 | — |
| Perchloroethylene | 96.5 | 98.0 | 98.5 | 99.0 |

The insecticidal properties of solutions IIIA, IIIB, IIIC and IIID were evaluated using adult cockroaches as the test species and glass as the test surface, as described in Example II. The treated glass panels were exposed, in duplicate, to cockroaches after 1, 3, 7 and 10 days.

The percent mortality of cockroaches exposed to the treated glass panels is summarized below:

|  | Insecticide Solution | | | |
| --- | --- | --- | --- | --- |
| Residue Age | IIIA | IIIB | IIIC | IIID |
| 1 day | 40 | 100 | 100 | 100 |
| 3 days | 10 | 100 | 100 | 100 |
| 7 days | 0 | 50 | 100 | 15 |
| 10 days | 0 | 0 | 15 | 0 |

The residue from the control insecticide solution IIID killed 15% of the exposed cockroaches after 7 days and was ineffective after 10 days, while the residue from insecticide solution IIIC, containing 0.5% of the solid polysiloxane copolymer, killed 100% of the exposed cockroaches after 7 days and 15% after 10 days. When the concentration of solid polysiloxane copolymer in the solution was increased to 1.0%, as in solution IIIB, the release of the insecticide was retarded so that after 7 days cockroach mortality was 50% and after 10 days the release was insufficient to kill cockroaches. When the siloxane copolymer concentration was increased to 2.5%, as in solution IIIA, insecticide release was so greatly retarded that only partial kills were obtained from the onset of the test period.

EXAMPLE IV

A solution containing 50 weight-% non-volatiles was prepared as follows:
  15 g. solid polysiloxane copolymer X2-5056 (3 wt-% OH)
  15 g. DC-200/1000 dimethylpolysiloxane fluid
  30 g. perchloroethylene The solid polysiloxane copolymer-polysiloxane fluid solution was mixed with a pyrethroid composition to yield an insecticide-containing solution which was compared with an additive-free pyrethroid composition for insecticidal behavior. The components of the test compositions were as follows:

|  | Insecticide Solution | | | |
| --- | --- | --- | --- | --- |
|  | IVA | IVB | IVC | IVD |
| Pyrethroids | 0.1 | 0.1 | 0.1 | 0.1 |
| Piperonyl butoxide | 0.5 | 0.5 | 0.5 | 0.5 |
| Petroleum distillate | 0.4 | 0.4 | 0.4 | 0.4 |
| X2-5056 | 0.25 | 0.5 | 0.25 | — |
| DC-200/1000 | 1.25 | 0.5 | 0.25 | — |
| Perchloroethylene | 96.5 | 98.0 | 98.5 | 99.0 |

The insecticidal properties of solutions IVA, IVB, IVC, and IVD were evaluated using adult cockroaches as the test species and glass as the test surface, as described in Example II. The treated glass panels were exposed, in duplicate, to cockroaches after 1, 3, 7 and 10 days.

The percent mortality of cockroaches exposed to the treated glass panels is summarized below:

|  | Insecticide Solution | | | |
| --- | --- | --- | --- | --- |
| Residue Age | IVA | IVB | IVC | IVD |
| 1 day | 100 | 100 | 100 | 100 |
| 3 days | 100 | 100 | 100 | 100 |
| 7 days | 80 | 55 | 15 | 15 |
| 10 days | 15 | 0 | 0 | 0 |

The residue from the control insecticide solution IVD killed 15% of the exposed cockroaches after 7 days and was ineffective after 10 days. The insecticide solution IVC containing 0.5% of the solid siloxane copolymer-polysiloxane fluid mixture was no more effective than the control. However, when the additive concentration was increased to 1.0%, the residue killed 55% of the cockroaches after 7 days. A further increase of the additive concentration to 2.5% controlled the pesticide release so that 80% of the cockroaches were killed after 7 days and 15% after 10 days.

What is claimed is:

1. A composition consisting essentially of (a) a solid organopolysiloxane, soluble in organic solvents, and containing hydroxyl groups, wherein the number of hydroxyl radicals ranges from 1 radical per polysiloxane molecule up to 30 weight percent of the total organopolysiloxane molecular weight, and (b) an insecticide, the amount of insecticide being from about 1 part by weight to 0.5 to 1,000 parts by weight of solid polysiloxane.

2. The composition of claim 1 wherein the organopolysiloxane contains the structural unit

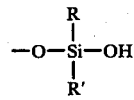

wherein R and R' are oxygen, hydrogen, hydrocarbon or heterocyclic radicals.

3. The composition of claim 2 wherein the hydrocarbon radicals are selected from the group consisting of branched, linear or cyclic aliphatic radicals, aromatic radicals, aralkyl radicals and alkylaryl radicals.

4. A composition consisting essentially of (a) a solid organopolysiloxane, soluble in organic solvents, and containing hydroxyl groups, wherein the number of hydroxyl radicals ranges from 1 radical per polysiloxane molecule up to 30 weight percent of the total organopolysiloxane molecular weight, (b) a non-volatile, non-reactive hydrocarbon oil or organopolysiloxane, and (c) an insecticide.

5. A composition consisting essentially of (a) a solid organopolysiloxane, soluble in organic solvents, and containing hydroxyl groups, wherein the number of hydroxyl radicals ranges from 1 radical per polysiloxane molecule up to 30 weight percent of the total organopolysiloxane molecular weight, (b) an insecticide, the amount of insecticide being from about 1 part by weight to 0.5 to 1,000 parts by weight of solid polysiloxane, and (c) a volatile diluent selected from the group consisting of aliphatic or aromatic hydrocarbons, halogenated hydrocarbons, organopolysiloxane fluids and water.

6. A composition consisting essentially of (a) a solid organopolysiloxane, soluble in organic solvents, and containing hydroxyl groups, wherein the number of hydroxyl radicals ranges from 1 radical per polysiloxane molecule up to 30 weight percent of the total organopolysiloxane molecular weight, (b) a non-volatile, non-reactive hydrocarbon oil or organopolysiloxane, (c) an insecticide, the amount of insecticide being from about 1 part by weight to 0.5 to 1,000 parts by weight of solid polysiloxane, and (d) a volatile diluent selected from the group consisting of aliphatic or aromatic hydrocarbons, halogenated hydrocarbons, organopolysiloxane fluids and water.

7. A process for providing a substrate containing active hydrogen atoms with an adherent controlled release pesticide which comprises applying the composition of claim 1 to said substrate and exposing the coated substrate to atmospheric moisture.

8. A process for providing a substrate containing active hydrogen atoms with an adherent controlled release pesticide which comprises applying the composition of claim 2 to said substrate and exposing the coated substrate to atmospheric moisture.

9. A process for providing a substrate containing active hydrogen atoms with an adherent controlled release pesticide which comprises applying the composition of claim 3 to said substrate and exposing the coated substrate to atmospheric moisture.

10. A process for providing a substrate containing active hydrogen atoms with an adherent controlled release pesticide which comprises applying the composition of claim 4 to said substrate and exposing the coated substrate to atmospheric moisture.

11. A process for providing a substrate containing active hydrogen atoms with an adherent controlled release pesticide which comprises applying the composition of claim 5 to said substrate and exposing the coated substrate to atmospheric moisture.

12. A process for providing a substrate containing active hydrogen atoms with an adherent controlled release pesticide which comprises applying the composition of claim 6 to said substrate and exposing the coated substrate to atmospheric moisture.

13. A process as defined in claim 7 wherein said substrate is a plant.

14. A process as defined in claim 7 wherein said substrate is an animal.

15. A process as defined in claim 7 wherein said substrate is the surface of a structure.

* * * * *